(12) United States Patent
Johnson et al.

(10) Patent No.: US 10,992,805 B1
(45) Date of Patent: Apr. 27, 2021

(54) DEVICE, SYSTEM AND METHOD FOR MODIFYING WORKFLOWS BASED ON CALL PROFILE INCONSISTENCIES

(71) Applicant: MOTOROLA SOLUTIONS, INC., Chicago, IL (US)

(72) Inventors: Eric Johnson, Chicago, IL (US); Preetam Pagar, Chicago, IL (US); Richard Mostaert, Chicago, IL (US); Mariya Bondareva, Chicago, IL (US)

(73) Assignee: MOTOROLA SOLUTIONS, INC., CHICAGO, IL (US)

( * ) Notice: Subject to any disclaimer, the term of this patent is extended or adjusted under 35 U.S.C. 154(b) by 0 days.

(21) Appl. No.: 16/752,913

(22) Filed: Jan. 27, 2020

(51) Int. Cl.
| | |
|---|---|
| H04M 3/51 | (2006.01) |
| G06Q 50/26 | (2012.01) |
| G16H 10/60 | (2018.01) |
| G10L 15/22 | (2006.01) |
| G10L 15/18 | (2013.01) |
| G06K 9/00 | (2006.01) |
| G06Q 10/06 | (2012.01) |
| G06K 9/72 | (2006.01) |

(52) U.S. Cl.
CPC ....... H04M 3/5116 (2013.01); G06K 9/00718 (2013.01); G06K 9/726 (2013.01); G06Q 10/06316 (2013.01); G06Q 10/063112 (2013.01); G06Q 50/265 (2013.01); G10L 15/1815 (2013.01); G10L 15/22 (2013.01); G16H 10/60 (2018.01); H04M 3/5133 (2013.01); H04M 2242/04 (2013.01)

(58) Field of Classification Search
CPC combination set(s) only.
See application file for complete search history.

(56) References Cited

U.S. PATENT DOCUMENTS

| | | | |
|---|---|---|---|
| 7,724,889 B2 | 5/2010 | Bushey et al. | |
| 8,238,532 B1 | 8/2012 | Cox et al. | |
| 10,276,190 B2 | 4/2019 | Ashoori et al. | |
| 2002/0002464 A1 | 1/2002 | Petrushin | |
| 2007/0208569 A1* | 9/2007 | Subramanian | G10L 19/0018 704/270 |
| 2013/0065628 A1* | 3/2013 | Pfeffer | G08B 25/016 455/521 |

(Continued)

FOREIGN PATENT DOCUMENTS

KR      101864824 B1      6/2018

*Primary Examiner* — Phung-Hoang J Nguyen
(74) *Attorney, Agent, or Firm* — Perry + Currier, Inc.

(57) ABSTRACT

A device, system and method for modifying workflows based on call profile inconsistencies is provided. A device monitors a call, received from a caller reporting an incident. The device performs one or more sentiment analysis and semantic analysis on one or more of: video of the caller on call; audio of the caller on call; and transcribed text of the audio of the call. The device determines a profile for the call, from a plurality of predetermined profiles stored at a memory accessible to the device, the plurality of predetermined profiles previously generated from historical data. In response to determining an inconsistency between the profile for the call and one or more of the sentiment analysis and the semantic analysis, the device determines a modified workflow for handling the call. The device provides, at a notification device, the modified workflow for handling the call reporting the incident.

18 Claims, 5 Drawing Sheets

(56) References Cited

U.S. PATENT DOCUMENTS

| | | |
|---|---|---|
| 2014/0169534 A1 | 6/2014 | Bentley et al. |
| 2015/0195406 A1 | 7/2015 | Dwyer et al. |
| 2017/0149972 A1* | 5/2017 | Klemm ............... H04M 3/5191 |
| 2018/0240028 A1 | 8/2018 | Baracaldo Angel et al. |
| 2018/0359654 A1* | 12/2018 | McDonald ............ H04W 76/50 |

* cited by examiner

DEVICE, SYSTEM AND METHOD FOR MODIFYING WORKFLOWS BASED ON CALL PROFILE INCONSISTENCIES

BACKGROUND OF THE INVENTION

In public safety and/or private security operations, call takers and/or dispatchers may need to make split-second decisions to ensure that the certain workflows are followed such that a correct responder gets to an incident scene.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

In public safety and/or private security operations, call takers and/or dispatchers may need to make split-second decisions to ensure that the certain workflows are followed such that a correct responder gets to an incident scene. However, as anyone may call a public safety call taker, and the like, and as callers may be injured, impaired, mischievous, bad actors, and the like, information provided by callers on calls, may not always reflect a correct fact scenario for an incident being reported. For example, a caller may be calling to report an accident and may themselves be injured, but may be unaware of the injury (e.g. due to shock, and the like). In another example, a caller may engage in "swatting" in an attempt to cause police, and the like, to be dispatched to an address where no incident has occurred. As such, a call taker, such as a 911 call taker, may follow a workflow for handling a call which causes an incorrect responder to be dispatched to an incident and/or the call taker may follow a work-flow for handling a call that inadequately responds to an incident.

Hence, provided herein is a device, system and method for modifying workflows based on call profile inconsistencies. In particular, a call-taking computing device, and the like, determines a profile for a call, such as an incident-type profile, a caller profile, and/or the like. For example, the call-taking computing device may determine that a call is reporting a minor traffic accident, and select and/or assign a minor traffic accident-type profile for the call, which may indicate that callers reporting a minor traffic accident exhibit a certain type of behavior on such a call. The call-taking computing device performs sentiment analysis and/or semantic analysis on audio and/or transcribed text of a call, for example to determine inconsistencies with the profile. Continuing with the minor traffic accident example, the caller may be speaking slowly and/or sluggishly, while the minor traffic accident-type profile indicates that callers reporting minor traffic accidents are excited and fast-talking. As such, the call-taking computing device may determine that the caller may be injured and determine a modified workflow for handling the call reporting the minor traffic accident; for example, a workflow for handling the call reporting a minor traffic accident may be to dispatch a police cruiser to the incident scene, whereas a modified workflow for handling the call by the caller may be to dispatch a police cruiser and an ambulance to the incident scene.

An aspect of the present specification provides a method comprising: monitoring, via a call-taking computing device, a call from a caller reporting an incident; performing, via the call-taking computing device, one or more of sentiment analysis and semantic analysis on one or more of: audio of the call; and transcribed text of the audio of the call; determining, via the call-taking computing device, a profile for the call, from a plurality of predetermined profiles stored at a memory accessible to the call-taking computing device, the plurality of predetermined profiles previously generated from historical data; in response to determining an inconsistency between the profile for the call and one or more of the sentiment analysis and the semantic analysis, determining, via the call-taking computing device, a modified workflow for handling the call; and providing, via the call-taking computing device, at a notification device, the modified workflow for handling the call.

Another aspect of the present specification provides a device comprising: a communication unit; and a controller configured to: monitor a call, received via the communication unit, from a caller reporting an incident; perform one or more of sentiment analysis and semantic analysis on one or more of: audio of the call; and transcribed text of the audio of the call; determine a profile for the call, from a plurality of predetermined profiles stored at a memory accessible to the controller, the plurality of predetermined profiles previously generated from historical data; in response to determining an inconsistency between the profile for the call and one or more of the sentiment analysis and the semantic analysis, determine a modified workflow for handling the call; and provide, at a notification device, the modified workflow for handling the call.

Figure 1:
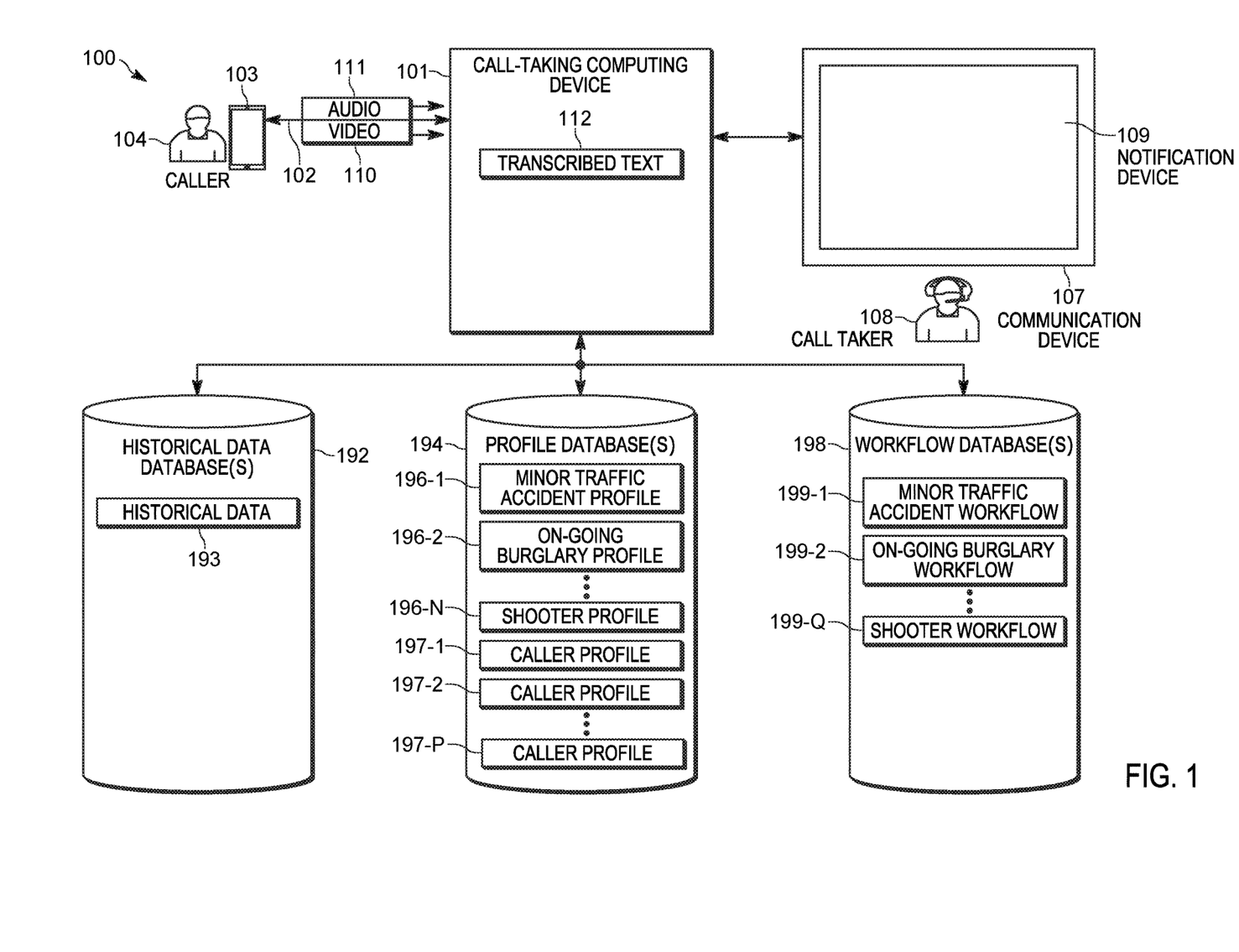
FIG. 1 is a system for modifying workflows based on call profile inconsistencies, in accordance with some examples.

Attention is directed to FIG. 1, which depicts an example system 100 for modifying workflows based on call profile inconsistencies. The system 100 comprises a computing device 101, which may comprise (e.g. as depicted) a call-taking computing device. The computing device 101, interchangeably referred to hereafter as the device 101, is generally configured to receive calls, for example, as depicted, a call 102 from a calling device 103 operated by a caller 104 who is generally calling to report an incident. While the device 101 is referred to as a call-taking computing device, however, the device 101 may be further configured to make calls. Hence, while the terms "call-taking computing device", "caller" and "calling device" are used throughout the present specification, a call-taking computing device may be configured to make out-going calls, a caller may be the recipient of such an outgoing call, for example using a calling device.

In some examples, the device 101 may comprise a public safety answering point (PSAP) computing device and/or a 911 computing device and/or a dispatcher computing device, and the like. However, the device 101 may comprise a call-taking device of a private security company, a business entity, and the like, and/or a call-taking device of any entity that may manage incidents and/or dispatch responders to incidents, whether public safety personnel (e.g. police officers, fire fighters, emergency medical technicians) and/or company employees and/or security guards, volunteers, and the like. However, hereafter the system 100, and components thereof, will be described with respect to public safety operations and/or a PSAP.

As depicted, the system 100 further comprises a communication device 107 in communication with the device 101 via a communication link (e.g. depicted as a double-ended arrow therebetween). As depicted, the communication device 107 may comprise a terminal and/or a dispatch terminal to which the device 101 forwards the call 102. The communication device 107 is generally operated by a human user, for example, as depicted, a call taker 108, such as a public safety and/or private security call taker, a 911 call taker, a dispatcher, and the like. The communication device 107 generally includes a notification device 109, as depicted a display screen; however the notification device 109 may include any suitable combination of one or more notification devices such as a display screen, a speaker, and the like.

As depicted, the calling device 103 comprises a mobile device, but the calling device 103 may comprise any suitable communication device for making a call to the device 101 including, but not limited to, the depicted mobile device, public switched telephone network (PSTN) telephones, laptops, personal computers, and the like. Furthermore, the call 102 may occur via any suitable wireless or wired network and may include, but are not limited to, mobile phone calls, PSTN calls, Internet Protocol (IP) calls, calls made using applications, and the like.

While one calling device 103 is depicted in FIG. 1, the system 100 may comprise any suitable number of calling devices 103 and associated callers 104; similarly, while one communication device 107 is depicted in FIG. 1, the system 100 may comprise any suitable number of communication devices 107 (e.g. dispatch terminals) and associated call takers 108 and/or human users.

The device 101 may be configured to receive the call 102, from the calling device 103 and the like, in association with a public safety answering point, a private security answering point center, a 911 answering point, and the like. For example, a communication device 107 may comprise a terminal of the PSAP, and a human user of a communication device 107 may comprise a call taker 108 of the PSAP.

However, as noted above, while present examples will be described with respect to a PSAP, the device 101 may be configured to receive calls 102 for any suitable type of answering point, dispatch center, and the like.

As depicted, for example, the caller 104 has operated the calling device 103 to initiate the call 102 using a number (e.g. "911") for the PSAP to report an incident. The device 101 automatically receives and/or answers the call 102 thereby causing a communication link between the device 101 and the calling device 103 to be generated using any suitable combination of wired and/or wireless networks. Communication links between components of the system 100 are depicted in FIG. 1, and throughout the present specification, as double-ended arrows between respective components; the communication links may include any suitable combination of wireless and/or wired links and/or wireless and/or wired communication networks. Hence, for example, communication links between the device 101 and the communication device 107 are generally established and the device 101 may forward and/or transfer the call 102 from the calling device 103 to the communication device 107 over such communication links.

As depicted, the caller 104 may be operating the calling device 103 to make the call 102 to the device 101 to report an incident using video 110 and/or audio 111 on the call 102 (e.g. speech spoken by the caller 104). In some examples, the audio 111 may be a component of the video 110 (e.g. the video 110 may comprise the audio 111, as an aural component, and a visual component). Indeed, hereafter, reference to the audio 111 may include the audio 111 being provided without the video 110 and/or the audio 110 being a component of the video 110, and/or the audio 111 may be provided without the video 110. However, the caller 104 may be incorrectly reporting the incident due to injury, impairment, and the like, and/or the caller 104 may be a bad actor and/or have malicious and mischievous intentions, and the like; in either situation, if the call taker 108 implements a workflow for responding to the incident being reported, based only on the words (e.g., based on the substantive content of the call 101, in some examples, however void of any other context or information) of the caller 104, incorrect responders may be dispatched to the incident and/or a response to the incident may be inadequate.

As understood herein, a workflow comprises a set of instructions and/or a policy and/or a script for handling a call reporting an incident and/or a given incident type. In some examples, once an incident type for a call is determined, for example automatically by the device 101 and/or by the call taker 108 speaking to the caller 104 and entering an incident type into a field of a graphic user interface at a display screen of the communication device 107, and the like, a workflow for handling a call for the incident type may be retrieved from a database of workflows and provided to the call taker 108 (e.g. at the display screen). Such workflows may include dispatching a given responder type to a location of the incident (e.g. as defined by a given policy), providing a given script for the call taker 108 to follow at a display screen of the communication device 107, and the like.

As will be described hereafter, the device 101 is generally configured to determine a profile for the call 102, and determine whether there is an inconsistency between the profile and one or more sentiment analysis and semantic analysis on the video 110 and/or audio 111 and/or transcribed text 112 of the video 110 and/or audio 111.

The term "sentiment", as described herein, may generally refer to an emotion and/or human feeling, and the like, of what a caller is saying and/or conveying on a call, independent of language being used by a caller, and which may be determined and/or derived and/or inferred from keywords, key phrases, idioms, orders of words, how ideas are expressed using words, and the like, used by a caller on a call and/or cadence of speech by the caller, speed of speech by the caller, frequencies of speech by the caller, tone of speech by the caller, inflection of speech by the caller, pitch of speech by the caller. Where the video 110 of the caller is available in the call 102, sentiment may also be determined via facial expression analysis, body language analysis, lip quiver analysis, etc. captured via video and identified via a corresponding video analytics algorithm and the like. In particular regard to the audio 111 (and/or audio of the video 110), in some examples, cadence, speed, frequencies, tone, inflection, and/or pitch, and the like, of speech and/or audio of the caller may be used to determine sentiment. Hence, the term "expected sentiment", as used herein, may refer to an expected emotional response and/or human feeling that a caller conveys on a call (e.g. expected sentiment of what a caller may say on a call). For example, a caller reporting a burglary may convey an emotion and/or sentiment of excitement and/or an emotion and/or sentiment of fear using any suitable keywords, key phrases, idioms, orders of words, and the like, and/or cadence, speed, frequencies, tone, inflection, and/or pitch, and the like, of speech and/or audio of the caller, and the like (e.g. which may be used to derive and/or infer sentiment and/or emotion). As will be described herein, actual sentiment of audio data on a call (e.g. emotion expressed by a caller on a call) for a given incident type may differ from the expected sentiment.

The term "semantics", as described herein, may generally refer to a meaning of what a caller is saying on a call, independent of language being used by a caller, and which may be determined and/or derived and/or inferred from keywords, key phrases, idioms, orders of words, how ideas are expressed using words, and the like, used by a caller on a call. Hence, the term "expected semantics", as used herein may refer to an expected meaning that a caller conveys on a call (e.g. expected semantics of what a caller may say on a call). For example, a caller reporting a burglary may convey a meaning of a burglary occurring and a meaning of concern about the burglary using any suitable keywords, key phrases, idioms, orders of words and the like, which may be used to derive and/or infer meaning. As will be described herein, actual semantics of audio data on a call (e.g. what a caller is saying on a call) for a given incident type may differ from the expected semantics. It is hence understood that, keywords, key phrases, idioms, orders of words and the like (e.g. of the audio 111 and/or the transcribed text 112), may be used to derive and/or infer sentiment and/or semantics on a call.

As depicted, the system 100 further comprises at least one historical data database 192 in communication with the device 101. The historical data database 192 may comprise any suitable database and/or memory, where historical data 193 is stored which may include historical data 193 associated with incidents, historical data 193 associated with caller 104, specifically, and the like. For example, the historical data 193 may include one or more of:

Previous call data (e.g. from and/or to the device 101 and/or similar devices). Such previous call data may comprise call records for calls reporting other incidents of the same type (e.g. from other callers) and/or a different type, and/or such previous call data may comprise call records for calls from the caller 104 and/or other callers. The previous call data may include indications of an expected emotional response and/or an expected sentiment and/or expected semantics of video data and/or audio data of a generic caller (e.g. what a generic caller is saying and/or visually expressing on a call as determined from audio and/or video and/or recorded audio and/or recorded video and/or transcribed text) for an incident type and/or for a particular caller. In some examples, the previous call data may include audio (e.g. recorded audio) and/or video (e.g. recorded video) and/or transcribed text of previous calls.

Other call data (e.g. from and/or to the device 101 and/or similar devices). Such other call data may be similar to the previous call data but may comprise records for any calls that may not be reporting incidents and/or may not be from the caller 104. The other call data may include indications of an expected emotional response and/or expected sentiment and/or expected semantics of a caller for an incident type and/or for a particular caller. In some examples, the other call data may include audio (e.g. recorded audio) and/or transcribed text of the other calls. A subset of one or more of the previous call data and the other call data may be from (and/or to) responders.

Computer-aided dispatch data. Such computer-aided dispatch data may comprise records of responders that were dispatched to previous incidents; such computer-aided dispatch data may hence include indications of incident type and the responders that were dispatched to incidents of the incident type and/or indications of incidents escalating to include other types of responders, rather than initially dispatched responders.

Records and/or police records. Such records and/or police records may comprise records generated by dispatchers, first responders, police officers, and the like, responding to incidents, and which may include indications of whether or not the responders dispatched to the incidents were adequate and/or whether other types of responders were summoned and/or dispatched to the incidents (e.g. after the police officers arrived and assessed the incidents). The records and/or police records may include indications of an expected emotional response and/or expected sentiment and/or expected semantics of what participants in an incident are saying, for example as recorded in the records and/or police records by police officers.

Incident resolution data. Such incident resolution data may comprise records generated by call takers, responders, and the like, which summarize incidents after incidents are resolved and/or responded to, and which may include indications of whether or not the responders dispatched to the incidents were adequate and/or whether other types of responders were summoned and/or dispatched to the incidents. The incident resolution data may include indications of an expected emotional response and/or expected sentiment and/or expected semantics of what participants in an incident are saying, for example as recorded in the incident resolution data by responders.

Evidence data. Such evidence data may comprise evidence gathered by responders responding to incidents. The evidence data may include, but is not limited to, digital evidence data, such as media content, call recordings and associated annotations, and the like, and/or digital indications of physical evidence. The evidence data may be stored in association with incidents. The evidence data may include indications of an expected emotional response and/or expected sentiment and/or expected semantics of what participants in an incident are saying, for example as recorded in the incident resolution data by responders.

Jail data. Such jail data may include records of previously incarcerated individuals, which may include the caller 104, and which may include indications of a history of their general expected emotional responses and/or expected sentiments and/or expected semantics (e.g. anger issues, addiction issues, etc.) and/or mental health and/or medical records.

Social media data. Such social media data may include social media posts of callers, which may include the caller 104, and which may include indications of a history of their expected emotional response and/or expected sentiment and/or expected semantics (e.g. which may indicate anger issues, addiction issues, etc.).

Medical records. Such medical records may be for callers, which may include the caller 104, and which may include indications of a history of callers' expected emotional response and/or expected sentiment and/or expected semantics (e.g. which may indicate anger issues, addiction issues, etc.).

Security records. Such security records may be similar to the police records, but may be records generated by security guards, and the like, responding to incidents (e.g. incidents to which the security guards responded, such as at a mall, a private home, a theme park, a sporting event, and the like, monitored by a private company which employs the security guards) as well as indications of incidents escalating, as described above.

Customer records. Such customer records may comprise records of customers of a private company, which may include the caller 104, which may include indications of a history of their expected emotional response and/or expected sentiment and/or expected semantics (a caller may often be excited, or a caller may often be calm, and/or an expected emotional response and/or expected sentiment and/or expected semantics may depend on an incident type).

Hence, in some examples, the historical data database 192 may comprise one or more of: an answering point database, a computer-aided dispatch database, a police records database, an incident resolution database, an evidence database, a jail database, a social media database, medical records database, a security records database, a customer database, and the like. Indeed, when the historical data database 192 includes databases operated by private companies, (e.g. a social media database operated by a social media company), the device 101 may have been has been granted access to such databases; alternatively, the device 101 may not have been granted access to private information at such databases but may access public information at such databases (e.g. public data on social media accounts, and the like). Indeed, any suitable historical data database 192 is within the scope of present examples.

As depicted, the system 100 further comprises one or more profile databases 194 storing a plurality of predetermined profiles 196-1, 196-2 . . . 196-N, 197-1, 197-2 . . . 197-P. The predetermined profiles 196-1, 196-2 . . . 196-N comprise incident-type profiles and the profiles 197-1, 197-2 . . . 197-P comprise caller profiles. Hereafter the plurality of predetermined profiles 196-1, 196-2 . . . 196-N, 197-1, 197-2 . . . 197-P are interchangeably referred to, collectively, as the profiles 196, 197 and, generically, as a profile 196, 197. However, the plurality of profiles 196-1, 196-2 . . . 196-N, may also interchangeably referred to, collectively, as the incident-type profiles 196 and, generically, as an incident-type profile 196; similarly, the plurality of profiles 197-1, 197-2 . . . 197-P, may also interchangeably referred to, collectively, as the caller profiles 197 and, generically, as a caller profile 197.

In some examples, the database 194 may store only incident-type profiles 196, while in other examples the database 194 may store only caller profiles 197. In yet further examples, a profile may store both incident-type profile data and caller profile data.

As depicted, there are an integer number "N" of incident-type profiles 196, each corresponding to a different incident type. The number "N" may be any suitable integer, including, but not limited to, a number of incident types that the device 101 has been trained, and/or configured, to recognize, for example on the basis of data and/or metadata and/or audio associated with previous incidents, for example as provided by the historical data 193. The number "P" may be any suitable integer, including, but not limited to, a number of callers that the device 101 has been trained, and/or configured, to recognize, for example on the basis of data and/or metadata and/or audio associated with previous incidents and/or calls that callers previously conducted with the device 101, and the like, for example as provided by the historical data 193.

In particular, the profiles 196, 197 may be generated from the historical data 193. The incident-type profile data 196 may generally indicate expected general behavior and/or an expected emotional response and/or expected sentiment and/or expected semantics of what callers reporting respective incident types may say on a call. For example, as depicted, the incident-type profile data 196 includes a minor traffic accident profile 196-1 which may indicate that callers reporting minor traffic accidents are generally excited, as indicated by the historical data 193. Similarly, as depicted, the incident-type profile data 196 includes an on-going burglary profile 196-2 which may indicate that callers reporting burglaries generally use quiet voices (e.g. so not to alert a burglar), as indicated by the historical data 193. Similarly, as depicted, the incident-type profile data 196 includes a shooter profile 196-N which may indicate that callers reporting shooters generally use loud, excited voices, as indicated by the historical data 193.

The caller profiles 197 may generally indicate behavior of specific and/or particular callers on calls. In particular, a caller profile 197 may be for a personally identifiable individual and/or a specific person. For example, the caller profile 197-1 may indicate that the caller 104 is usually very loud and excited on a call, regardless of what is being reported. The other caller profiles 197 may be for other callers and may indicate an emotional response and/or sentiment and/or semantics on a call, and which may be associated with a particular incident type. However, in other examples, a caller profile 197 may indicate that a respective caller is usually impaired and/or intoxicated when calling and/or a caller profile 197 may indicate that a respective caller is usually angry and/or excited when calling. In yet further examples, a caller profile 197 may indicate whether a respective caller has history of prank calls and/or mischievous calls, and the like, and/or whether a caller 197 has a history of violent behavior, and the like.

In some examples, the profiles 196, 197 may comprise classifiers, and the like, used by one or more machine learning algorithms, and the like, to classify a call to (and/or from) the device 101.

As depicted, the system 100 further comprises one or more workflow databases 198 storing, for example, workflows 199-1, 199-2 . . . 199-Q for different incident types. The plurality of workflows 199-1, 199-2 . . . 199-Q, may also interchangeably referred to, collectively, as the workflows 199 and, generically, as a workflow 199. As depicted, there are an integer number "Q" of workflows 198, each corresponding to a different incident type. The number "Q" may be any suitable integer, including, but not limited to, a same or different number of incident types that the device 101 has been trained, and/or configured, to recognize; however, the number "Q" of workflows 199 may be greater than the number "N" of incident-type profiles 196, less than the number "N" of incident-type profiles 196, or same as the number "N" of incident-type profiles 196. In still further examples, there may be "P" number of caller-type sub-workflow profiles for each of the "N" number of primary incident-type workflow profiles (e.g., that map to a particular combination of incident profile and caller profile combination). In still other examples, a single primary incident-type workflow profile may be identified as a default one for a particular incident type (e.g. assuming no inconsistencies in sentiment and/or semantics are detected relating to the incident and/or the caller 104), and subsequently detected inconsistencies in sentiment and/or semantics may cause a different sub-workflow profile (for the same type of incident) to be selected in place of the default as a function of the detected inconsistency (e.g., whether it is a detected semantic inconsistency, sentiment inconsistent, incident inconsistency, caller inconsistency, or some combination of two or more of the foregoing). Other variations and/or examples are possible as well.

Hence, as will be explained in more detail below, the device 101 may receive and transfer the call 102 to the communication device 107. The device 101 may further monitor the call 102 to determine a profile for the call 102, for example by selecting a profile 196, 197 from the plurality of predetermined profiles 196, 197 stored at a memory (e.g. the database 194) accessible to the call-taking computing device 101, the plurality of predetermined profiles 196, 197 previously generated from the historical data 193. The device 101 may further perform one or more of sentiment analysis and semantic analysis on the video 110 and/or audio 111 and/or the transcribed text 112 of the video 110 and/or audio 111 (e.g. generated using a speech-to-text engine). When the device 101 determines there is an inconsistency between the profile 196, 197 that has been determined, and one or more the sentiment analysis and the semantic analysis, the device 101 may determine a modified workflow for handling the call 102 reporting the incident, and provide the modified workflow at the notification device 109 and/or another notification device. For example when the caller 104 is reporting a minor traffic accident, sentiment analysis and/or semantic analysis on the video 110 and/or audio 111 and/or the transcribed text 112 thereof, may not be inconsistent with the minor traffic accident profile 196-1. The sentiment analysis and/or semantic analysis on the video 110 and/or audio 111 and/or the transcribed text 112 thereof may further indicate that the caller 104 is injured. Hence, the minor traffic accident workflow 199-1 may be modified to include dispatch of emergency medical technician to the incident being reported, in addition to police officers.

Figure 2:
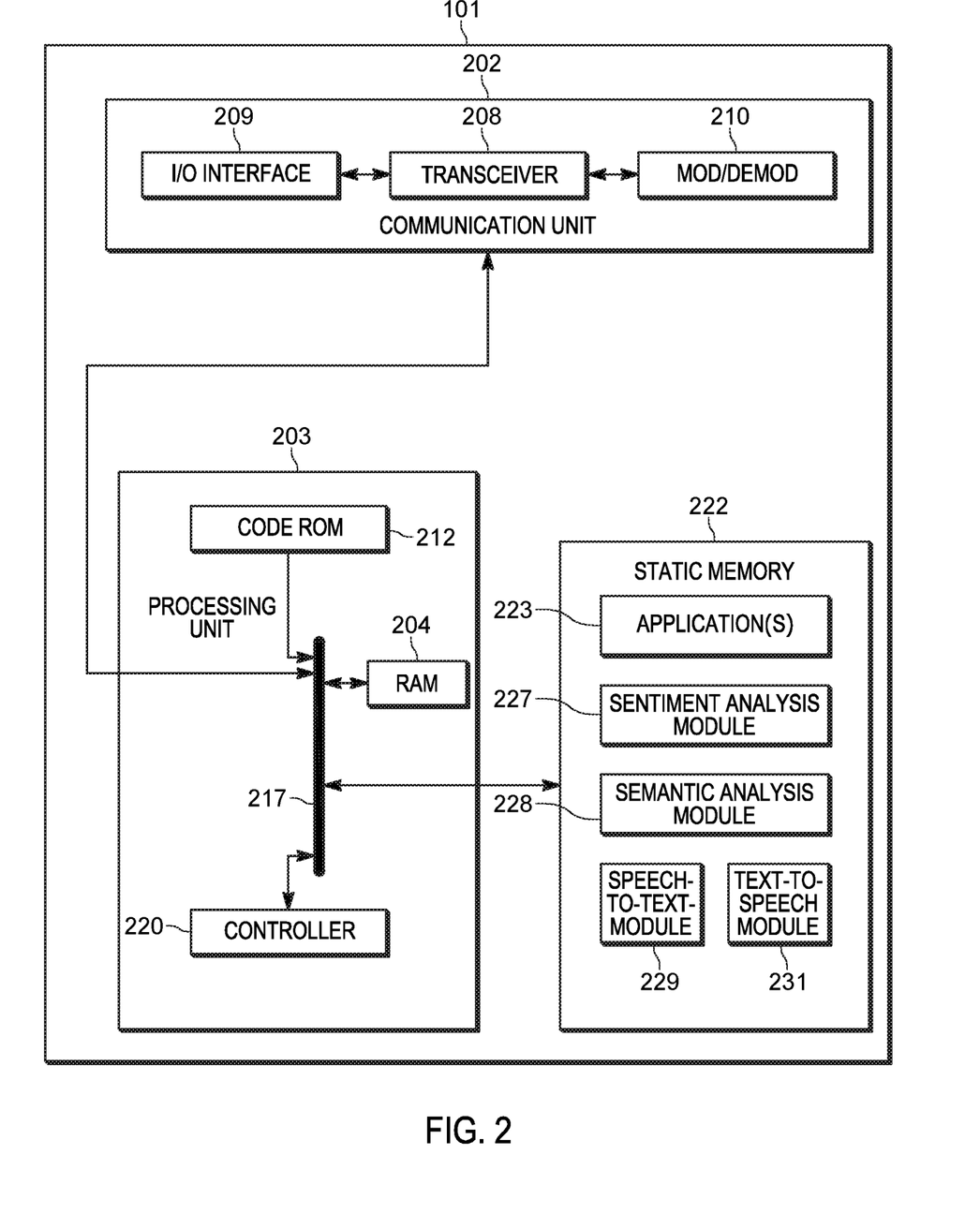
FIG. 2 is a device diagram showing a device structure of computing device for modifying workflows based on call profile inconsistencies, in accordance with some examples.

Attention is next directed to FIG. 2 which depicts a schematic block diagram of an example of the device 101. In general, the device 101 may comprise one or more servers and/or one or more cloud computing devices, and the like, configured to communicate with the calling device 103 and the communication device 107. However, the device 101 may comprise a computing device such as a personal computer and/or a laptop computer, and the like. In some examples, the device 101 may be combined with the communication device 107. The device 101 may be located at a PSAP, and the like, and/or remote from a PSAP, and the like. Similarly, the device 101 may be located at a same facility (e.g. a PSAP) as the communication device 107, and the like, and/or the device 101 and the communication device 107 may be remote from each other; indeed, the communication device 107 may be remote from a PSAP, and the like.

As depicted, the device 101 comprises: a communication unit 202, a processing unit 203, a Random-Access Memory (RAM) 204, one or more wireless transceivers 208, one or more wired and/or wireless input/output (I/O) interfaces 209, a combined modulator/demodulator 210, a code Read Only Memory (ROM) 212, a common data and address bus 217, a controller 220, and a static memory 222 storing at least one application 223. Hereafter, the at least one application 223 will be interchangeably referred to as the application 223.

While not depicted, the device 101 may include one or more of an input device and a display screen and the like, a microphone (e.g. to receive voice commands) such that a user, such as the call taker 108, may interact with the device 101. However, a user, such as the call taker 108, may interact with the device 101 via the communication device 107 which may include an input device (not depicted).

As shown in FIG. 2, the device 101 includes the communication unit 202 communicatively coupled to the common data and address bus 217 of the processing unit 203.

The processing unit 203 may include the code Read Only Memory (ROM) 212 coupled to the common data and address bus 217 for storing data for initializing system components. The processing unit 203 may further include the controller 220 coupled, by the common data and address bus 217, to the Random-Access Memory 204 and the static memory 222.

The communication unit 202 may include one or more wired and/or wireless input/output (I/O) interfaces 209 that are configurable to communicate with the calling device 103 and the communication device 107. For example, the communication unit 202 may include one or more transceivers 208 and/or wireless transceivers for communicating with the calling device 103 and/or the communication device 107. Hence, the one or more transceivers 208 may be adapted for communication with one or more communication networks used to communicate with the calling device 103 and/or the communication device 107. For example, the one or more transceivers 208 may be adapted for communication with one or more of the Internet, a digital mobile radio (DMR) network, a Project 25 (P25) network, a terrestrial trunked radio (TETRA) network, a Bluetooth network, a Wi-Fi network, for example operating in accordance with an IEEE 802.11 standard (e.g., 802.11a, 802.11b, 802.11g), an LTE (Long-Term Evolution) network and/or other types of GSM (Global System for Mobile communications) and/or 3GPP (3rd Generation Partnership Project) networks, a 5G network (e.g. a network architecture compliant with, for example, the 3GPP TS 23 specification series and/or a new radio (NR) air interface compliant with the 3GPP TS 38 specification series) standard), a Worldwide Interoperability for Microwave Access (WiMAX) network, for example operating in accordance with an IEEE 802.16 standard, and/or another similar type of wireless network. Hence, the one or more transceivers 208 may include, but are not limited to, a cell phone transceiver, a DMR transceiver, P25 transceiver, a TETRA transceiver, a 3GPP transceiver, an LTE transceiver, a GSM transceiver, a 5G transceiver, a Bluetooth transceiver, a Wi-Fi transceiver, a WiMAX transceiver, and/or another similar type of wireless transceiver configurable to communicate via a wireless radio network.

The communication unit 202 may optionally include one or more wireline transceivers 208, such as an Ethernet transceiver, a USB (Universal Serial Bus) transceiver, or similar transceiver configurable to communicate via a twisted pair wire, a coaxial cable, a fiber-optic link, or a similar physical connection to a wireline network. The transceiver 208 is also coupled to a combined modulator/demodulator 210.

The controller 220 may include ports (e.g. hardware ports) for coupling to other hardware components.

The controller 220 may include one or more logic circuits, one or more processors, one or more microprocessors, and/or the controller 220 may include one or more ASIC (application-specific integrated circuits) and one or more FPGA (field-programmable gate arrays), and/or another electronic device. In some examples, the controller 220 and/or the device 101 is not a generic controller and/or a generic device, but a device specifically configured to implement functionality for modifying workflows based on call profile inconsistencies. For example, in some examples, the device 101 and/or the controller 220 specifically comprises a computer executable engine configured to implement functionality for modifying workflows based on call profile inconsistencies.

The static memory 222 is a non-transitory machine readable medium that stores machine readable instructions to implement one or more programs or applications. Example machine readable media include a non-volatile storage unit (e.g. Erasable Electronic Programmable Read Only Memory ("EEPROM"), Flash Memory) and/or a volatile storage unit (e.g. random-access memory ("RAM")). In the example of FIG. 2, programming instructions (e.g., machine readable instructions) that implement the functional teachings of the device 101 as described herein are maintained, persistently, at the memory 222 and used by the controller 220 which makes appropriate utilization of volatile storage during the execution of such programming instructions.

As depicted, the memory 222 further stores a sentiment analysis module 227 and/or a semantic analysis module 229, speech-to-text module 229 and a text-to-speech module 231, which may be used by the device 101 and/or the controller 220 while implementing the application 223.

The sentiment analysis module 227 may be configured to analyze the video 110 and/or audio 111, for example based on facial expression analysis, body language analysis, lip quiver analysis cadence of the video 110, and/or speed and/or frequencies and/or tone and/or inflection and/or pitch of the audio 111, to determine an emotional response and/or sentiment of the caller 104 on the call 102. The sentiment analysis module 227 may be further configured to analyze sentiment of the transcribed text 112 of the video 110 and/or audio 111, which may include, but is not limited to, determining sentiment associated keywords, key phrases, and the like.

Similarly, the semantic analysis module 228 may be configured to analyze the video 110 and/or audio 111 and/or the transcribed text 112 to determine language-independent meaning of video 110 and/or audio 111 and/or the transcribed text 112. For example, the semantic analysis module 228 may be used to determine a meaning and/or idea being conveyed by caller 104 on the call 102 based keywords, key phrases, orders of words, idioms, how ideas are expressed using words, and the like, and which may be independent of emotion being conveyed by the caller 104. In some examples, the modules 227, 228 may be combined.

As such, the speech-to-text module 229 may be to convert the audio 111 on the call 102 to the transcribed text 112 for analysis by the sentiment analysis module 227 and/or the semantic analysis module 228.

The text-to-speech module 231 may be to convert text to audio for example in examples where the device 101 provides notifications in the form of sound (e.g. at a speaker of the communication device 107), and the like.

Figure 3:
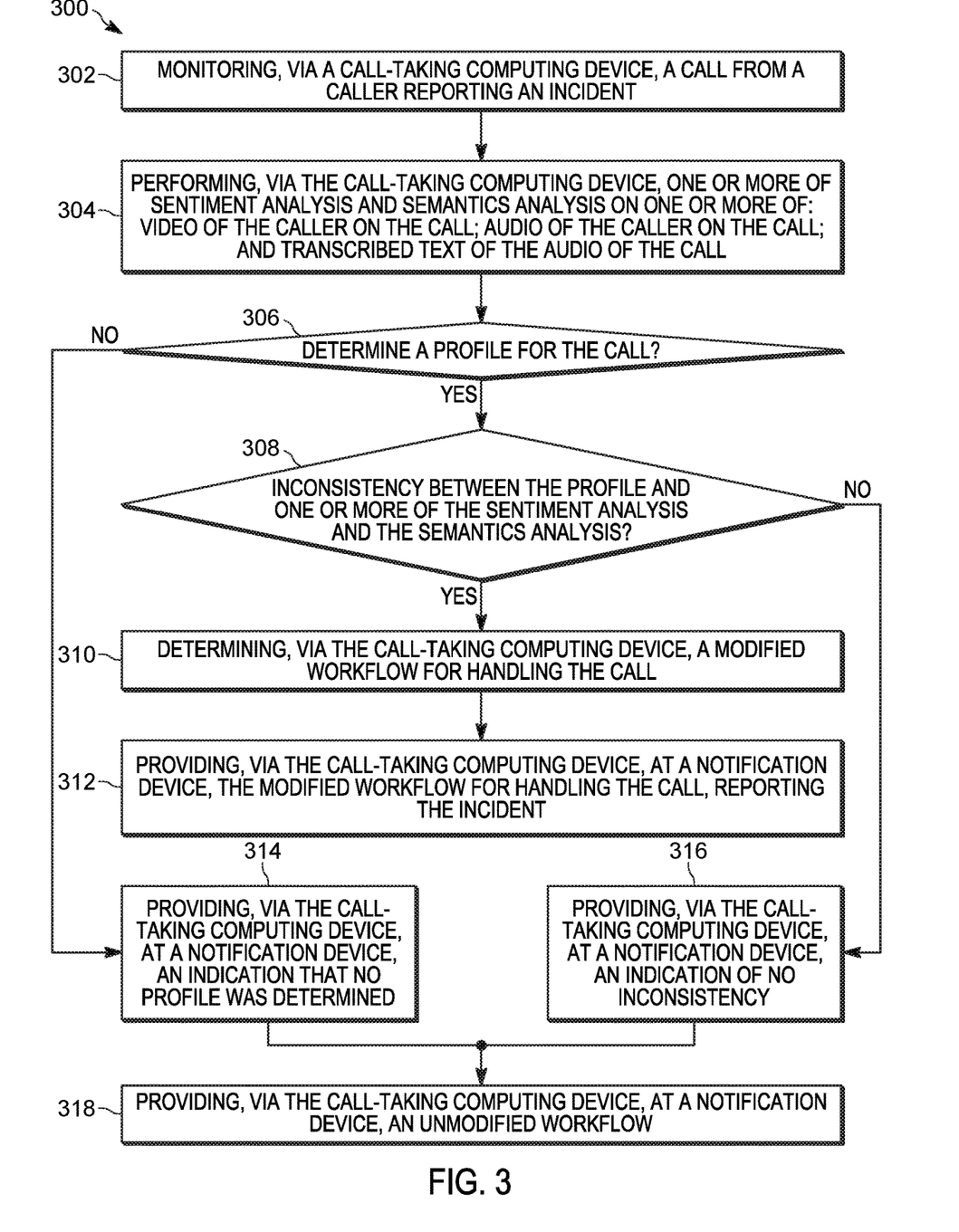
FIG. 3 is a flowchart of a method for modifying workflows based on call profile inconsistencies, in accordance with some examples.

In particular, the memory 222 stores instructions corresponding to the at least one application 223 (and which may include the modules 227, 228, 229, 231) that, when executed by the controller 220, enables the controller 220 to implement functionality described herein including, but not limited to, the blocks of the method set forth in FIG. 3.

In illustrated examples, when the controller 220 executes the one or more applications 223, the controller 220 is enabled to: monitor a call from a caller reporting an incident; perform one or more of sentiment analysis and semantic analysis on one or more of: video of the caller on the call; audio of the caller on the call; and transcribed text of the audio of a call; determine, a profile for the call, from a plurality of predetermined profiles stored at a memory accessible to the call-taking computing device, the plurality of predetermined profiles previously generated from historical data; in response to determining an inconsistency between the profile for the call and one or more the sentiment analysis and the semantic analysis, determine a modified workflow for handling the call; and provide, at a notification device, the modified workflow for handling the call, reporting the incident.

The application 223 and/or the sentiment analysis module 227 and/or the semantic analysis module 228 may include numerical algorithms configured to perform sentiment analysis and/or semantic analysis on one or more of: video of a call; audio of a call; and transcribed text of audio of a call. Similarly, the application 223 may include numerical algorithms configured to one or more of: determine, a profile for a call, from a plurality of predetermined profiles (e.g. the profiles 196, 197); determine an inconsistency between a profile for a call and one or more of sentiment analysis and semantic analysis on a call; and determine a modified workflow for an incident.

Alternatively, and/or in addition to numerical algorithms, the application 223 and/or the sentiment analysis module 227 and/or the semantic analysis module 228 may include machine learning models and/or algorithms, and the like, which have been trained to perform sentiment analysis and/or semantic analysis on one or more of: video of a call; audio of a call; and transcribed text of audio of a call. Similarly, the application 223 may include machine learning models and/or algorithms, and the like, which have been trained to one or more of: determine, a profile for a call, from a plurality of predetermined profiles; determine an inconsistency between a profile for a call and one or more of sentiment analysis and semantic analysis on a call; and determine a modified workflow for an incident.

Furthermore, in these examples, the application 223 and/or the sentiment analysis module 227 and/or the semantic analysis module 228 may initially be operated by the controller 220 in a training mode to train the machine learning models and/or algorithms of the application 223 to perform the above described functionality.

In yet further examples, the application 223 may be operated in one or more of a profile generating and/or profile updating mode to one or more of generate and/or update the profiles 196, 197, for example based on the historical data 193.

The one or more machine learning models and/or algorithms of the application 223 may include, but are not limited to: a deep-learning based algorithm; a neural network; a generalized linear regression algorithm; a random forest algorithm; a support vector machine algorithm; a gradient boosting regression algorithm; a decision tree algorithm; a generalized additive model; evolutionary programming algorithms; Bayesian inference algorithms, reinforcement learning algorithms, and the like. However, generalized linear regression algorithms, random forest algorithms, support vector machine algorithms, gradient boosting regression algorithms, decision tree algorithms, generalized additive models, and the like may be preferred over neural network algorithms, deep learning algorithms, evolutionary programming algorithms, and the like, in some public safety environments, such as a 911 answering point. Any suitable machine learning algorithm and/or deep learning algorithm and/or neural network is within the scope of present examples.

In examples where the application 223 includes one or more machine learning algorithms, the profiles 196, 197 may include classifiers, and the like, used by the one or more machine learning algorithms to determine a profile of the call 102.

While details of the calling device 103 and the communication device 107 are not depicted, the calling device 103 and the communication device 107 may have components similar to the device 101 adapted, however, for the functionality of the calling device 103 and the communication device 107. For example, the calling device 103 and/or the communication device 107 may include respective display screens (e.g. such as the notification device 109 as depicted), speakers, microphones, location determining devices (e.g. GPS devices), and the like.

Attention is now directed to FIG. 3, which depicts a flowchart representative of a method 300 for modifying workflows based on call profile inconsistencies. The operations of the method 300 of FIG. 3 correspond to machine readable instructions that are executed by the device 101, and specifically the controller 220 of the device 101. In the illustrated example, the instructions represented by the blocks of FIG. 3 are stored at the memory 222 for example, as the application 223. The method 300 of FIG. 3 is one way in which the controller 220 and/or the device 101 and/or the system 100 may be configured. Furthermore, the following discussion of the method 300 of FIG. 3 will lead to a further understanding of the system 100, and its various components.

The method 300 of FIG. 3 need not be performed in the exact sequence as shown and likewise various blocks may be performed in parallel rather than in sequence. Accordingly, the elements of method 300 are referred to herein as "blocks" rather than "steps." The method 300 of FIG. 3 may be implemented on variations of the system 100 of FIG. 1, as well.

At a block 302, the controller 220 and/or the device 101 monitors the call 102 from the caller 104 reporting an incident (e.g. and more specifically from the calling device 103). For example, the call 102 may be answered by the device 101 and the video 110 and/or audio 111 on the call 102 may be automatically responded to by the device 101, at least initially, via the text-to-speech engine 231 (e.g. and a script, not depicted, used by the device 101). Alternatively, the call 102 may be answered by the device 101 and transferred to the communication device 107; the call taker 108 and the caller 104 may talk on the call 102 and the device 101 may monitor their conversation. Such monitoring may include, but is not limited to, one or more of: monitoring the video 110 and/or audio 111, recording the video 110 and/or audio 111, transcribing the audio 111 to generate the transcribed text 112 (e.g. using the speech-to-text engine 229), and the like.

At a block 304, the controller 220 and/or the device 101 performs one or more of sentiment analysis and semantic analysis on one or more of: the video 110 of the caller 104 on the call 102; audio 111 of the caller 104 on the call 102; and the transcribed text 112 of the audio 111 of the call 102 (e.g. when generated). The sentiment analysis may generally be performed using the sentiment analysis module 227 and may include, but is not limited to, determining a sentiment for the call 102, based on the video 110 and/or audio 111 and/or the transcribed text 112. The semantic analysis may generally be performed using the semantic analysis module 228 and may include, but is not limited to, determining semantics for the call based on the transcribed text 112. The sentiment and/or the semantics may indicate a response and/or an emotional response of the caller 104, such as whether the caller 104 is excited, calm, has slurred words, is joking, is nervous, a meaning and/or ideas being conveyed by the caller 104 (which may not different from an emotional response) and the like.

At a block 306, the controller 220 and/or the device 101 determines whether a profile 196, 197 for the call 102 may be determined, from the plurality of predetermined profiles 196, 197 stored at a memory (e.g. the database 194) accessible to the call-taking computing device 101, the plurality of predetermined profiles 196, 197 previously generated from the historical data.

As described above, the predetermined profiles 196, 197 may comprise classifiers, and the like, used by the one or more machine learning algorithms of the application 223 to determine a profile of the call 102 based, for example on the video 110 and/or audio 111 of the call 102 and/or the transcribed text 112 (e.g. when generated) and/or metadata for the call 102 (e.g. which may include a location of an incident being reported), and the like. Alternatively, the transcribed text 112 may be used to attempt to generate a profile for the call 102 (e.g. an estimate of an incident type for the call and/or an estimate of a name and/or identify of the caller 103) which may be compared with the profiles 196, 197 to determine a match and/or an approximate match, between an estimated profile for the call 102 and the profiles 196, 197.

As described above, a profile for the call 102, for example as determined at the block 306, may comprise one or more of an incident-type profile 196 associated with the incident being reported on the call 102, and a caller profile 197 associated with the caller 104.

In particular examples, the controller 220 and/or the device 101 may determine and/or attempts to determine, an incident-type profile 196 for the call 102 at the block 306, rather than a caller profile 197. Indeed, in these examples, the caller profiles 197 may be reserved and/or dedicated for determining a modified workflow for handling the call 102, as described in more detail below. In general, a profile determined at the block 306 may indicate an expected emotional response and/or expected sentiment and/or expected semantics of the caller 104 on the call 102, for example based on the incident-type profile 196 of the incident type being reported on the call 102.

In some examples, the controller 220 and/or the device 101 may determine a profile for the call 102 by selecting a profile 196, 197 from the plurality of predetermined profiles 196, 197 and/or by matching data and/or metadata associated with the call 102 to data of the plurality of predetermined profiles 196, 197 (e.g. selecting a profile 196, 197 that matches and/or about matches a profile 196, 197 from the plurality of predetermined profiles 196, 197).

In response to the controller 220 and/or the device 101 determining a profile for the call 102 (e.g. a "YES" decision at the block 306), at a block 308, the controller 220 and/or the device 101 determines whether there is an inconsistency between the profile (e.g. as determined at the block 306), for the call 102 and one or more of the sentiment analysis and the semantic analysis (e.g. as performed at the block 304).

For example, determining the inconsistency may comprise one or more of: determining a respective variation between semantics, determined from the semantic analysis (e.g. of the transcribed text 112 when generated), and expected semantics associated with the profile for the call 102 (e.g. one of the profiles 196, 197), as determined at the block 306; and determining a difference between a sentiment, determined from the sentiment analysis, and an expected sentiment associated with the profile for the call 102, as determined at the block 306. In other words, determining the inconsistency may comprise determining a respective variation between one or more of sentiment and semantics and expected sentiment and/or expected semantics associated with the profile for the call 102.

In response to determining an inconsistency between the profile for the call 102 and one or more of the sentiment analysis and the semantic analysis (e.g. a "YES" decision at the block 308), at a block 310, the controller 220 and/or the device 101 determines a modified workflow for handling the call 102. For example, an unmodified workflow 199 for an incident type for the profile determined at the block 306 may be selected from the workflows 199, and modified based on the inconsistency determined at the block 308. In some examples, determining the modified workflow for handling the call 102 may be based, at least in part on a type of the inconsistency. In particular, the inconsistency may indicate that a caller 102 may be injured based, for example, on the caller 102 speaking quietly and/or slurring their words when the profile determined at the block 306 indicates that callers reporting the incident type of the incident being reported on the call 102 are generally expected to be excited. Hence, the type of inconsistency may be indicative of a medical condition of the caller 102. However, the type of inconsistency may indicate that the caller 102 is lying and/or that the caller 102 is a bad actor, that the caller 102 is trying to cause mischief (e.g. via swatting) and the like, and the modified workflow for handling the call 102 may be determined and/or generated accordingly, for example by dispatching more and/or different responders to a location of an incident being reported and/or a determined location of the caller 102 (e.g. using automatic location identification (ALI) functionality of the device 101).

In some examples, determining the modified workflow for handling the call 102 may be based, at least in part on a caller profile 197. For example, when the profile determined at the block 306 comprises an incident-type profile 196 such that the incident type of the incident being reported has been determined, and a caller profile 197-1 for the caller 104 is found at the database 194, the caller profile 197-1 may indicate a medical condition for the caller 104.

In a particular example, the caller profile 197-1 may indicate that the caller 104 has a heart condition and may require an ambulance and/or emergency medical technicians, even though the caller 104 is not reporting that they are having heart problems; hence the modified workflow for handling the call 102 may include dispatching an emergency medical technicians to the location of the caller 104 (e.g. in addition to dispatching police officers to a location of an incident the caller 104 is reporting).

In another example, the caller profile 197-1 may indicate a history of the caller 104 reporting false information (e.g. swatting), and hence the modified workflow for handling the call 102 may include dispatching a police unit to the location of the caller 104 (e.g. rather than a location of an incident the caller 104 is reporting).

In yet another example, the caller profile 197-1 may indicate that the caller 104 calls the device 101 often (e.g. above a threshold rate of calling) and, when the caller 104 calls, they are always very agitated, and the calls usually and/or always (e.g., above a threshold probability) turn out to be false. Hence, when the caller 104 sentiment analysis and/or the semantic analysis indicates that the caller 103 is not agitated (e.g. inconsistent with the caller profile 197-1), then a modified workflow for handling the call 102 may include modifying a workflow 199 to check on the caller 104 as their behavior, for example in addition to dispatching a responder to a location of the incident being reported, as their behavior is inconsistent with usual behavior of the caller 104.

Hence, in particular examples, a profile for the call 102, as determined at the block 306, may comprise an incident-type profile 196 associated with the incident being reported on the call, the inconsistency, as determined at the block 308, may be based on the incident-type profile 197, and determining, at the block 310, the modified workflow for handling the call 102 may be based on a caller profile 197 associated with the caller 104.

In general, the modified workflow for handling the call 102 may comprise a workflow 199 modified to address the determined inconsistency. However, the modified workflow for handling the call 102 may comprise a workflow 199 modified to address the determined inconsistency may comprise a newly generated workflow (e.g. generated using machine learning algorithms, and the like).

At a block 312, the controller 220 and/or the device 101 provides at a notification device, the modified workflow for handling the call 102 (e.g. reporting the incident), as determined at the block 310.

The notification device of the block 312 may comprise a terminal, and/or a display screen and/or speaker thereof (e.g. the notification device 109 of the communication device 107), operated by the call taker 108 on the call 102. However, in some examples, the notification device of the block 312 may comprise a communication device of a responder dispatched to respond to the incident.

When the notification device of the block 312 comprises a terminal (e.g. the notification device 109 of the communication device 107), and the like, operated by the call taker 108 on the call 102, and an unmodified workflow 199 for handling the call 102 comprises dispatching a given responder type to the incident, the modified workflow for handling the call 102, as determined at the block 310, may comprise at least one of: dispatching a different responder type in addition to the given responder type of the unmodified workflow 199; and dispatching the different responder type in place of the given responder type. For example, emergency medical technicians may be dispatched in addition to, or instead of, police officers.

In further examples, when the notification device of the block 312 comprises a terminal, and the like, operated by the call taker 108 on the call 102, and an unmodified workflow 199 for handling the call 102 comprises providing the call taker 108 with a given script at the terminal, the modified workflow for handling the call 102 may comprise: providing the call taker 108 with a modified script to obtain data related to the inconsistency (e.g. to ask questions about medical conditions, and the like).

In yet further examples, the notification device of the block 312 may comprise a communication device (e.g. a mobile device), and the like, of a responder dispatched to the incident of the call 102, and an unmodified workflow 199 for handling the call 102 may comprise providing the responder with a given set of tactics for handling the incident. In these examples, the modified workflow for handling the call 102 may comprise: providing the responder with modified tactics (e.g. to be more or less aggressive when responding to the incident).

Returning briefly to the block 306, in response to the controller 220 and/or the device 101 being unable to determine a profile for the call 102 (e.g. a "NO" decision at the block 306), at an optional block 314, the controller 220 and/or the device 101 provides at a notification device (e.g. the notification device 109), an indication that no profile could be determined. Put another way, the block 314 may include the controller 220 and/or the device 101 failing to determine a profile for the call 102.

Similarly, returning briefly to the block 308, in response to the controller 220 and/or the device 101 being unable to determine an inconsistency between the profile for the call 102 and one or more the sentiment analysis and the semantic analysis (e.g. a "NO" decision at the block 308), at an optional block 316, the controller 220 and/or the device 101 provides at a notification device (e.g. the notification device 109), an indication of no inconsistency. Put another way, the block 316 may include the controller 220 and/or the device 101 being determining a consistency between the profile for the call 102 and one or more of the sentiment analysis and the semantic analysis.

Regardless of a "NO" decision at the block 306 and/or the block 308, and regardless of whether or not the block 314 and/or the block 316 is implemented, at block 318, the controller 220 and/or the device 101 may provide, at a notification device, an unmodified workflow for handling the call 102. However, the block 318 may also be optional.

Put another way, the method 300 may include the controller 220 and/or the device 101, in response to one or more of: failing to determine a predetermined profile for the call 102 (e.g. at the block 306); and determining (e.g. at the block 308) a consistency between the profile for the call 102 and one or more of the sentiment analysis and the semantic analysis: providing, at a notification device (e.g. the notification device 109), one or more of: an unmodified workflow for handling the call 102 (e.g. at the block 318), and a notification of one or more of: the failing (e.g. at the block 314); and the consistency (e.g. at the block 316).

As mentioned above, the historical data 193 may be used to generate the profiles 196, 197. However, any data obtained on the call 102 and/or associated with the call 102 (e.g. call data, computer-aided dispatch data, police records, incident resolution data, and the like) may be used to generate and/or update the profiles 196, 197. Similarly, any other calls to the device 101, either before, during or after the call 102, may be used to generate and/or update the profiles 196, 197. For example, any data obtained on the call 102 and/or associated with the call 102 and/or other calls, may be stored in the historical data 193 and used to generate and/or update the profiles 196, 197. Put another way, the method 300 may further comprise the controller 220 and/or the device 101 one or more of generating and updating the plurality of predetermined profiles 196, 197 based on one or more of data obtained in association with the call 102 and the historical data 193.

An example of the method 300 will next be described with respect to FIG. 4 and FIG. 5, which are similar to FIG. 1 with like components having like numbers.

Figure 4:
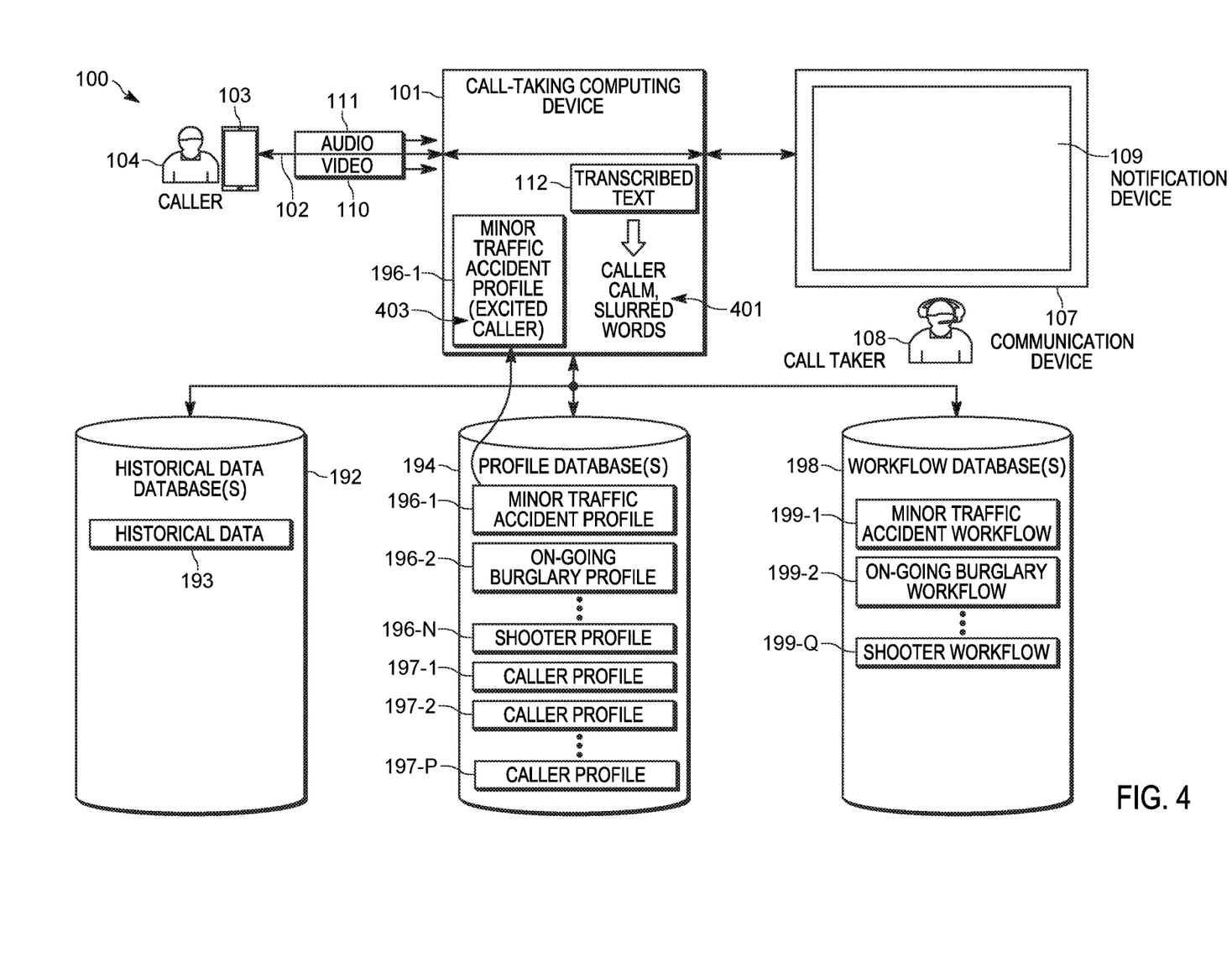
FIG. 4 depicts an example of a method for modifying workflows based on call profile inconsistencies implemented in the system of FIG. 1, in accordance with some examples.

Attention is next directed to FIG. 4 which depicts the call 102 being transferred from the calling device 103 to the communication device 107 for example via the device 101, as indicated in FIG. 4 by a communication link (e.g. a double ended arrow) within the device 101. However, it is understood that the transfer of the call 102 from the calling device 103 to the communication device 107 may occur in any suitable manner that enables the device 101 to monitor the call 102 (e.g. at the block 302 of the method 300).

As also depicted in FIG. 4, the device 101 has performed sentiment analysis and/or semantic analysis on the call 102 (e.g. at the block 304 of the method 300) and determined an emotional response and/or sentiment and/or semantics 401 of the caller 102 on the call 102; for example, as depicted, the emotional response and/or sentiment and/or semantics 401 indicate that the caller 102 is calm and is slurring their words (e.g. as determined from the transcribed text 112).

As also depicted in FIG. 4, the device has determined (e.g. at the block 306 of the method 300) an incident-type profile 196-1 for the call 102. In particular, the device 101 has determined that the caller 104 is reporting a minor traffic accident and hence the minor traffic accident profile 196-1 has been selected and/or determined as the profile for the call 102. As depicted in FIG. 4, the minor traffic accident profile 196-1 indicates that an expected emotional response and/or expected sentiment and/or expected semantics 403 of a caller reporting a minor traffic accident comprises the caller being excited (e.g. expected emotional response and/or expected sentiment and/or expected semantics 403 comprises "Excited Caller"). Hence, the device 101 compares the emotional response and/or sentiment and/or semantics 401 identified on the call 102 with the expected emotional response and/or expected sentiment and/or expected semantics 403 of the minor traffic accident profile 196-1 to determine (e.g. at the block 308 of the method 300) an inconsistency therebetween (e.g. the caller 102 is not "Excited" but "Calm" with slurred words).

Figure 5:
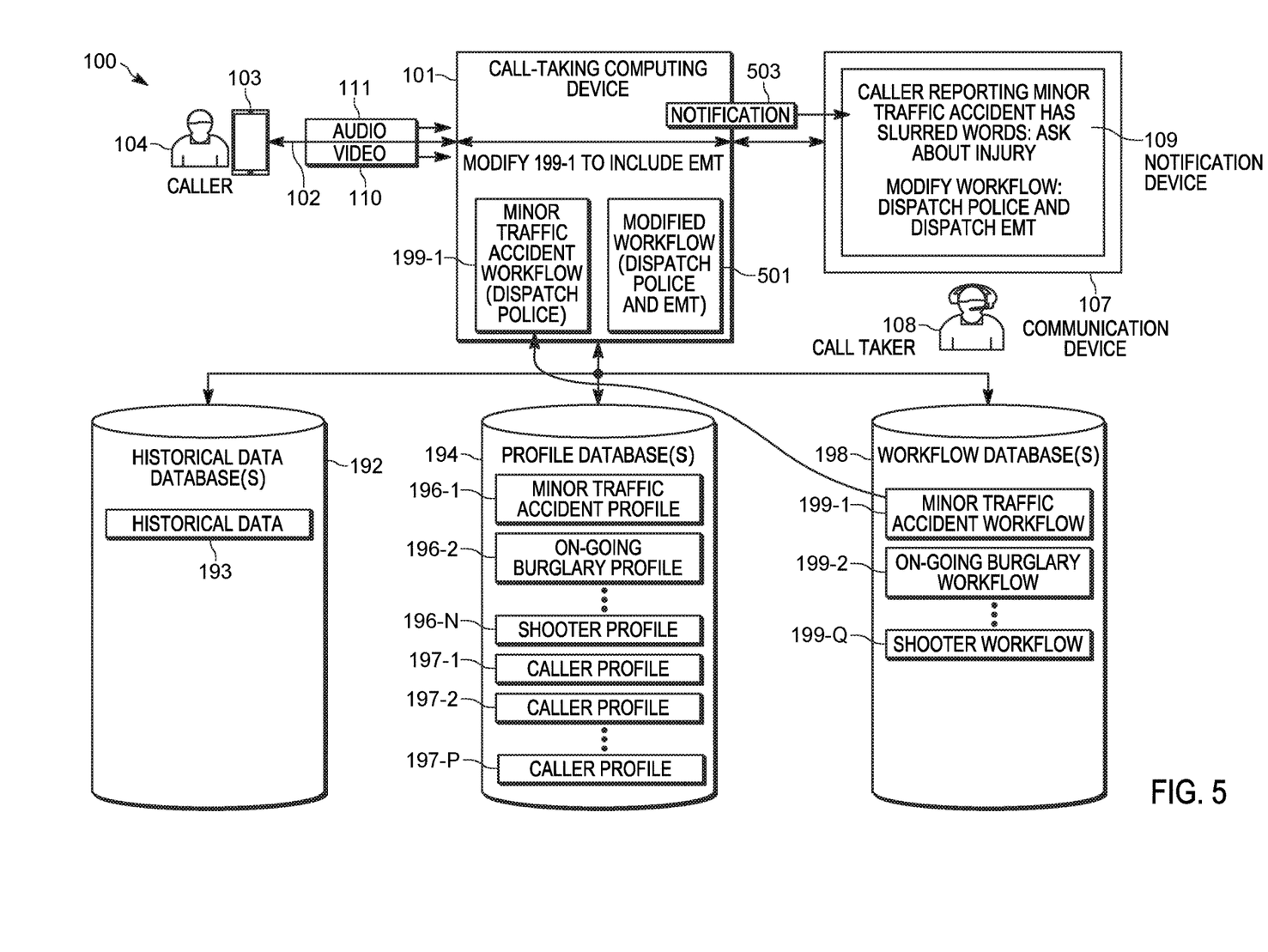
FIG. 5 depicts further aspects of the method for modifying workflows based on call profile inconsistencies implemented in the system of FIG. 1, in accordance with some examples.

Attention is next directed to FIG. 5 in which the device 101 has retrieved the minor traffic accident workflow 199-1 as the incident type for the call 102 has been identified as a "Minor Traffic Accident", as also indicated by the minor traffic accident profile 196-1 determined for the call 102. However the device 101 modifies the minor traffic accident workflow 199-1 to determine and/or generate (e.g. at the block 310 of the method 300) a modified workflow 501. As depicted, the minor traffic accident workflow 199-1 is modified from dispatching police only to the incident being report, to generate the modified workflow 501 where police and an emergency medical technician ("EMT") are both dispatched.

As also depicted in FIG. 5, the device 101 provides a notification 503 to the notification device 109 to control the notification device 109 to provide (e.g. at the block 312 of the method 300) the modified workflow 501. For example, as depicted, the notification device 109 comprises a display screen which provides text indicating that the caller 102 is reporting a minor traffic accident but has slurred words (e.g. and/or is calm) and that the call taker 108 is to implement the modified workflow 501 to dispatch police and an emergency medical technician. Furthermore, a script is modified and/or provided to prompt the call taker 108 to ask about an injury on the call 102; put another way, the modified script may be a component of the modified workflow 501.

While examples of the block 314, the block 316 and the block 318 are not depicted, it is understood that when a profile 196, 197 cannot be determined and/or no inconsistency is found, the notification device 109 may be controlled accordingly, as described above.

While the method 300 has been described with respect to a minor traffic accident, the method 300 may be used in conjunction with other incident types.

For example, a caller may call the device 101 reporting that his house is burglarized, and that the burglar is inside the house. The caller may be agitated and loud which may be inconsistent with a burglary incident-type profile where callers are generally quiet. A profile for the caller may then be used to determine that, when this caller was agitated, additional dispatch of EMTs occurred. Hence the inconsistency between the caller's determined emotional response and an expected emotional response for calls reporting burglaries leads to a modified workflow for handling the call, for example as based on the caller's profile.

In another example, a caller may call the device 101 reporting that his neighbor is playing loud music. The caller may be quiet which may be inconsistent with a loud music incident-type profile where callers are generally loud and aggressive, hence an inconsistency is determined. A profile for the caller may then be used to determine that this caller often makes calls in an impaired state; hence a modified workflow for handling the call may be generated to warn a responder about the impairment (e.g. when dispatching a responder).

In another example, a caller may call the device 101 and then hang up before information can be collected from the caller (e.g. an abandoned call). A call taker (e.g. the call taker 108) may return the abandoned call, and a "caller" answering the returned call made by the call taker may be quiet and apologetic, which may be inconsistent with an abandoned call incident-type profile where callers are generally loud and more aggressively apologetic, hence an inconsistency is determined. Hence, a modified workflow for handling the call may be generated to warn a responder the caller's behavior is inconsistent with abandoned calls (e.g. and the caller may not be the person who made the original abandoned call, and hence may be a bad actor).

In another example, a caller may call the device 101 reporting a shooting in an attempt to dispatch a SWAT (special weapons and tactics) team to a location. The caller may be quiet which may be inconsistent with a shooter incident-type profile where callers are generally loud and scared, hence an inconsistency is determined. A profile for the caller and/or a history of swatting attempts (e.g. as stored in the historical data 193) may then be used to determine that the call may be swatting attempt; hence a modified workflow for handling the call may be generated to warn dispatch police to the location of the caller rather than (and/or in addition to) the location of the reported shooting. In some examples, the device 101 may identify available video feeds (e.g. closed-circuit television (CCTV) video feeds) that originate at one or more of the location of the caller and the location of the reported shooting and provide the video feeds at the notification device 109; such video feeds may allow the call taker 108 to ask questions to the caller about the location of the caller and/or the reported shooting that someone who is not physically at the location could not answer (e.g. "What color is the house?"), for example to verify information reported by the caller and/or to catch the caller in falsehoods. Furthermore, a modified workflow could include providing a swatting attempt script at the notification device 109 to assist the call taker 108 in gathering evidence against the caller 104 and/or to attempt to get the caller 104 to entrap themselves (e.g. in the event the call is determined to be a swatting attempt).

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

In this document, language of "at least one of X, Y, and Z" and "one or more of X, Y and Z" may be construed as X only, Y only, Z only, or any combination of two or more items X, Y, and Z (e.g., XYZ, XY, YZ, XZ, and the like). Similar logic may be applied for two or more items in any occurrence of "at least one . . . " and "one or more . . . " language.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment may be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A method comprising:
   monitoring, via a call-taking computing device, a call from a caller reporting an incident of a given incident type;
   performing, via the call-taking computing device, one or more of sentiment analysis and semantic analysis on one or more of: video of the caller on the call; audio of the caller on the call; and transcribed text of the audio of the caller on the call;
   selecting, via the call-taking computing device, using the given incident type, an incident-type profile for the call, from a plurality of predetermined incident-type profiles associated with different incident types, including the given incident type, the plurality of predetermined incident-type profiles stored at a memory accessible to the call-taking computing device, the plurality of predetermined incident-type profiles previously generated from historical data comprising one or more of data, metadata and audio of previous calls associated with previous incidents of the different incident types;
   in response to determining an inconsistency between the incident-type profile for the call and one or more of the sentiment analysis and the semantic analysis, determining, via the call-taking computing device, a modified workflow for handling the call; and
   providing, via the call-taking computing device, at a notification device, the modified workflow for handling the call, reporting the incident.

2. The method of claim 1, wherein determining the inconsistency comprises one or more of:
   determining a respective variation between semantics, determined from the semantic analysis, and expected semantics associated with the incident-type profile for the call; and
   determining a difference between a sentiment, determined from the sentiment analysis, and an expected sentiment associated with the incident-type profile for the call.

3. The method of claim 1, wherein determining the modified workflow for handling the call is based on a caller profile associated with the caller.

4. The method of claim 1, wherein determining the modified workflow for handling the call is based, at least in part on a type of the inconsistency.

5. The method of claim 1, wherein the notification device comprises one or more of a terminal operated by a call taker on the call and a communication device of a responder dispatched to respond to the incident.

6. The method of claim 1, wherein the notification device comprises a terminal operated by a call taker on the call and an unmodified workflow for handling the call comprises dispatching a given responder type to the incident, and
   wherein the modified workflow for handling the call comprises at least one of:
   dispatching a different responder type in addition to the given responder type; and
   dispatching the different responder type in place of the given responder type.

7. The method of claim 1, wherein the notification device comprises a terminal operated by a call taker on the call and an unmodified workflow for handling the call comprises providing the call taker with a given script at the terminal, and
   wherein the modified workflow for handling the call comprises: providing the call taker with a modified script to obtain data related to the inconsistency.

8. The method of claim 1, further comprising:
   in response to one or more of: failing to determine a predetermined incident-type profile for the call; and determining a consistency between the incident-type profile for the call and one or more of the sentiment analysis and the semantic analysis: providing, at the notification device, one or more of: an unmodified workflow for handling the call, and a notification of one or more of: the failing; and the consistency.

9. The method of claim 1, further comprising one or more of generating and updating the plurality of predetermined incident-type profiles based on one or more of data obtained in association with the call and the historical data, the historical data further comprising one or more of:
   previous call data;
   other call data;
   computer-aided dispatch data;
   police records;
   incident resolution data;
   evidence data;
   jail data;
   social media data;
   medical records;
   security records; and
   customer records.

10. A device comprising:
a communication unit; and
a controller configured to:
monitor a call, received via the communication unit, from a caller reporting an incident of a given incident type;
perform one or more of sentiment analysis and semantic analysis on one or more of: video of the caller on the call; audio of the caller on the call; and transcribed text of the audio of the call;
select, using the given incident type, an incident-type profile for the call, from a plurality of predetermined incident-type profiles associated with different incident types, including the given incident type, the plurality of predetermined incident-type profiles stored at a memory accessible to the controller, the plurality of predetermined incident-type profiles previously generated from historical data comprising one or more of data, metadata and audio of previous calls associated with previous incidents of the different incident types;
in response to determining an inconsistency between the incident-type profile for the call and one or more of the sentiment analysis and the semantic analysis, determine a modified workflow for handling the call; and
provide, at a notification device, the modified workflow for handling the call, reporting the incident.

11. The device of claim 10, wherein the controller is further configured to determine the inconsistency by one or more of:
determining a respective variation between semantics, determined from the semantic analysis, and expected semantics associated with the incident-type profile for the call; and
determining a difference between a sentiment, determined from the sentiment analysis, and an expected sentiment associated with the incident-type profile for the call.

12. The device of claim 10, wherein
the controller is further configured to determine the modified workflow for handling the call based on a caller profile associated with the caller.

13. The device of claim 10, wherein the controller is further configured to determine the modified workflow for handling the call based, at least in part on a type of the inconsistency.

14. The device of claim 10, wherein the notification device comprises one or more of a terminal operated by a call taker on the call and a communication device of a responder dispatched to respond to the incident.

15. The device of claim 10, wherein the notification device comprises a terminal operated by a call taker on the call and an unmodified workflow for handling the call comprises dispatching a given responder type to the incident, and
wherein the modified workflow for handling the call comprises at least one of:
dispatching a different responder type in addition to the given responder type; and
dispatching the different responder type in place of the given responder type.

16. The device of claim 10, wherein the notification device comprises a terminal operated by a call taker on the call and an unmodified workflow for handling the call comprises providing the call taker with a given script at the terminal, and
wherein the modified workflow for handling the call comprises: providing the call taker with a modified script to obtain data related to the inconsistency.

17. The device of claim 10, wherein the controller is further configured to:
in response to one or more of: failing to determine a predetermined incident-type profile for the call; and determining a consistency between the incident-type profile for the call and one or more of the sentiment analysis and the semantic analysis: provide, at the notification device, one or more of: an unmodified workflow for handling the call, and a notification of one or more of: the failing; and the consistency.

18. The device of claim 10, wherein the controller is further configured to one or more of generate and update the plurality of predetermined profiles based on one or more of data obtained in association with the call and the historical data, the historical data further comprising one or more of:
previous call data;
other call data;
computer-aided dispatch data;
police records;
incident resolution data;
evidence data;
jail data;
social media data;
medical records;
security records; and
customer records.

* * * * *